United States Patent [19]
Leyde

[11] Patent Number: 6,119,039
[45] Date of Patent: Sep. 12, 2000

[54] METHOD AND APPARATUS FOR DELIVERING DEFIBRILLATION ENERGY

[75] Inventor: Kent W Leyde, Redmond, Wash.

[73] Assignee: Heartstream, Inc., Seattle, Wash.

[21] Appl. No.: 09/239,010

[22] Filed: Jan. 28, 1999

[51] Int. Cl.$^7$ .................................................. A61N 1/39
[52] U.S. Cl. ................................................................ 607/5
[58] Field of Search .............................. 607/5, 4, 7, 74

[56] References Cited

U.S. PATENT DOCUMENTS

| | | |
|---|---|---|
| 4,504,773 | 3/1985 | Suzuki et al. . |
| 4,637,397 | 1/1987 | Jones et al. . |
| 4,745,923 | 5/1988 | Winstrom . |
| 4,998,531 | 3/1991 | Bocchi et al. . |
| 5,078,134 | 1/1992 | Hellman et al. . |
| 5,111,816 | 5/1992 | Pless et al. . |
| 5,249,573 | 10/1993 | Fincke et al. . |
| 5,472,454 | 12/1995 | Ozawa . |
| 5,716,381 | 2/1998 | Reggiardo ..................................... 607/5 |
| 5,891,172 | 4/1999 | Stendahl et al. ............................ 607/5 |

FOREIGN PATENT DOCUMENTS

| | | |
|---|---|---|
| WO/93/16759 | 9/1993 | WIPO . |
| WO/94/22530 | 10/1994 | WIPO . |

*Primary Examiner*—Kennedy Schaetzle
*Attorney, Agent, or Firm*—Cecily Anne Snyder

[57] ABSTRACT

An automatic external defibrillator ("AED") is described that includes a high voltage delivery circuit for producing a biphasic electrical pulse to defibrillate a patient. The delivery circuit includes a plurality of capacitors controlled by IGBTs. The bridge circuit has four SCRs which are selectively switched to produce, for example, a biphasic steering of current.

7 Claims, 3 Drawing Sheets

METHOD AND APPARATUS FOR DELIVERING DEFIBRILLATION ENERGY

TECHNICAL FIELD

This invention relates to a method and apparatus for delivering electrical energy produced by a defibrillator to a patient experiencing ventricular fibrillation ("VF"). This invention provides a way to use switching devices, with a voltage rating lower than the overall voltage used by the system, to control the voltage delivery and facilitate voltage sharing. This invention may be used with either implantable or external defibrillators.

BACKGROUND OF THE INVENTION

Each day thousands of Americans are victims of cardiac emergencies. Cardiac emergencies typically strike without warning, oftentimes striking people with no history of heart disease. The most common cardiac emergency is sudden cardiac arrest ("SCA"). It is estimated that more than 1000 people per day are victims of SCA in the United States alone.

SCA occurs when the heart stops pumping blood. Usually SCA is due to abnormal electrical activity in the heart, resulting in an abnormal rhythm (arrhythmia). One such abnormal rhythm, VF, is caused by abnormal and very fast electrical activity in the heart. During VF the heart cannot pump blood effectively. Because blood may no longer be pumping effectively during VF, the chances of surviving decrease with time after the onset of the emergency. Brain damage can occur after the brain is deprived of oxygen for four to six minutes.

VF may be treated by applying an electric shock to the patient's heart through the use of a defibrillator. The shock clears the heart of the abnormal electrical activity (in a process called "defibrillation") by depolarizing a critical mass of myocardial cells to allow spontaneous organized myocardial depolarization to resume.

External defibrillators send electrical pulses to the patient's heart through electrodes applied to the patient's torso. External defibrillators are typically located and used in hospital emergency rooms, operating rooms, and emergency medical vehicles. Of the wide variety of external defibrillators currently available, automatic and semi-automatic external defibrillators (AEDs) are becoming increasingly popular because they can be used by relatively inexperienced personnel. Such defibrillators can also be especially lightweight, compact, and portable. One drawback to current defibrillator designs is the limited availability of high-voltage semiconductors to control voltage delivery. Although SCRs can tolerate a wide range of voltages, they do not turn off readily, which is a desirable feature when delivering a defibrillation energy pulse.

What is needed, therefore, is a defibrillator which can use a collection of widely available switching devices, which have a higher on/off responsiveness, to deliver a high voltage pulse, wherein the switching devices have a voltage rating lower than the overall voltage delivered by the system.

SUMMARY OF THE INVENTION

An electrical energy delivery circuit is provided for defibrillating a patient experiencing VF. The delivery circuit includes a storage circuit for storing electrical energy and having first and second terminals. A steering circuit is coupled with the first terminal of the storage circuit. The steering circuit is for coupling with the patient to transfer the electrical energy stored in the storage circuit to the patient. The storage circuit is comprised of a plurality of series capacitors which are controlled by a series of lower voltage switching devices connected in parallel to the capacitors. The lower voltage switching devices are, for example, IGBTs. By providing lower voltage switching devices, a number of advantages are achieved over conventional defibrillator circuit designs.

DETAILED DESCRIPTION OF THE INVENTION

Currently available external defibrillators provide either a monophasic or biphasic electrical pulse to a patient through electrodes applied to the chest. Monophasic defibrillators deliver an electrical pulse of current in one direction. Biphasic defibrillators deliver an electrical pulse of current first in one direction and then in the opposite direction. When delivered external to the patient, these electrical pulses are high energy (typically in the range of 30 J to 360 J). This invention may be employed by defibrillators that generate monophasic, biphasic or multiphasic waveforms. Additionally this invention may be employed by defibrillators that allow the user to select the waveform type. Finally, this invention may be employed in either external or implantable defibrillators.

Defibrillators employing a monophasic waveform are well known in the art. While this invention may be used with a defibrillator employing a monophasic waveform, it is believed that the solution described herein is primarily beneficial for defibrillators that deliver biphasic or multiphasic waveforms. An example of a circuit used for discharging a capacitor delivering a monophasic waveform is described in U.S. Pat. No. 4,504,773 (Suzuki et al.).

In accordance with the present invention, embodiments of defibrillators are provided that have a high voltage bridge circuit using only four switching elements to steer the biphasic pulse. In the following description, certain specific details are set forth in order to provide a thorough understanding of embodiments of the present invention. It will be clear, however, to one skilled in the art, that the present invention can be practiced without these details. In other instances, well-known circuits have not been shown in detail in order to avoid unnecessarily obscuring the description of the various embodiments of the invention. Also not presented in any great detail are those well-known control signals and signal timing protocols associated with the internal operation of defibrillators.

Figure 1:
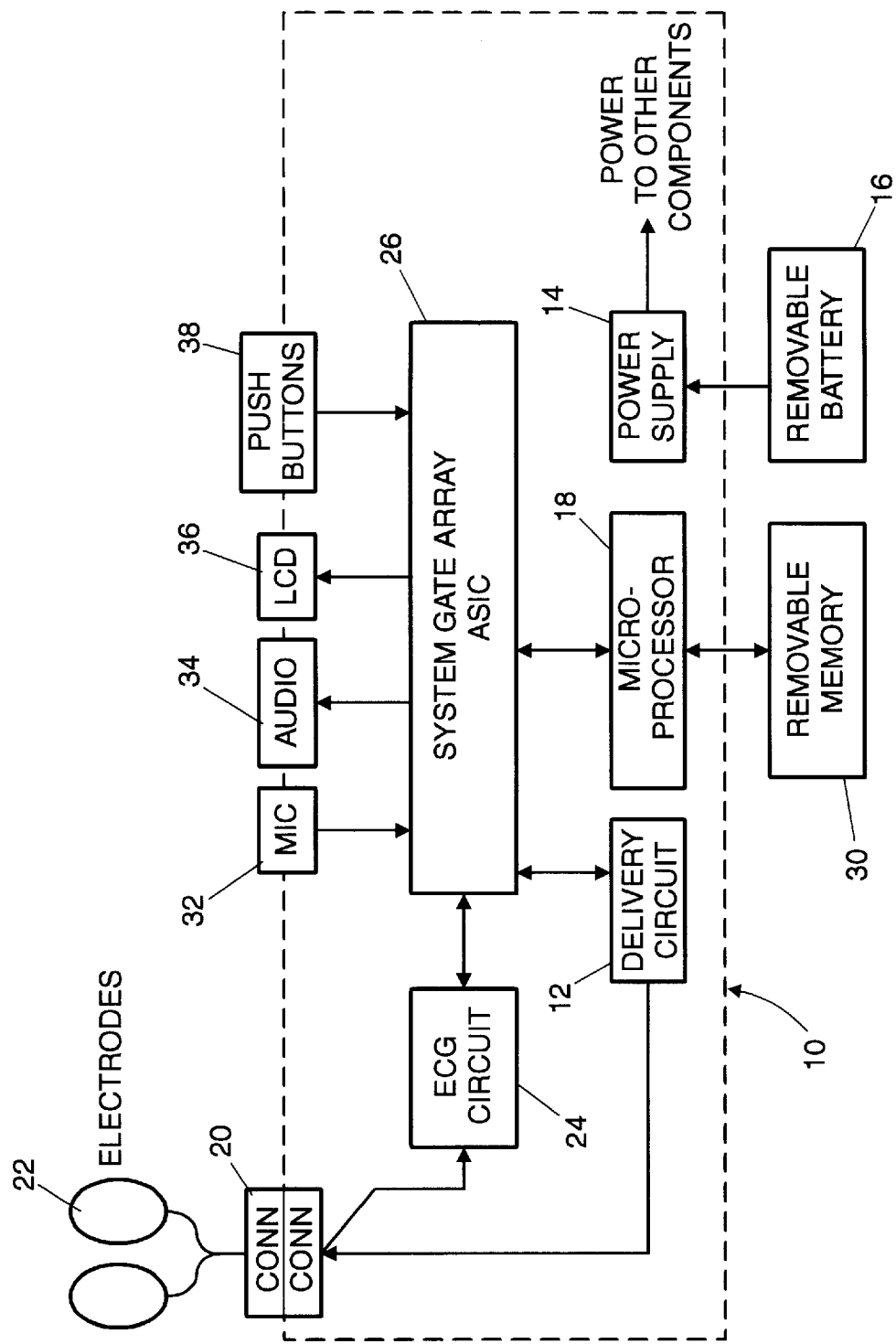
FIG. 1 is a functional block diagram depicting an external defibrillator according to an embodiment of the present invention.

FIG. 1 is a functional block diagram depicting a defibrillator or AED 10 having a delivery circuit 12, capable of delivering high or low voltage, depending upon the application, in accordance with an embodiment of the present invention. The AED 10 includes a power supply 14, which is powered by an energy source such as a removable battery 16 and provides power to other components of the AED. A microcontroller or processor 18 controls the operation of the various components of the AED 10. The high-voltage delivery circuit 12 delivers a pulse of electrical energy to a patient via an electrode connector or interface 20 and electrodes 22.

An electrocardiogram (ECG) circuit 24 acquires and processes the patient's ECG signals through the electrodes 22 and sends the signals to the processor 18 via a system gate array 26. The system gate array 26 is a custom application-specific integrated circuit (ASIC) integrating many of the defibrillator functions (including user interface control and many of the internal functions) and interfacing the processor 18 with other components of the AED 10. Providing the separate system gate array or ASIC 26 allows the processor 18 to focus on other tasks. Of course, the functionality of the ASIC 26 could be included within the operations performed by the processor 18, or could be replaced by discrete logic circuit components or a separately dedicated processor.

The AED 10 also includes a memory device 30 (such as a removable Personal Computer Memory Card International Association ("PCMCIA") card or magnetic tape), and user interface components such as a microphone 32, an audio speaker 34, an LCD display panel 36, and a set of push-button controls 38. Those skilled in the art will understand that a number of other components are included within the AED 10 (e.g., a system monitor and associated status indicators), but are not shown in order to avoid unnecessarily obscuring the description of embodiments of the invention.

Figure 2:
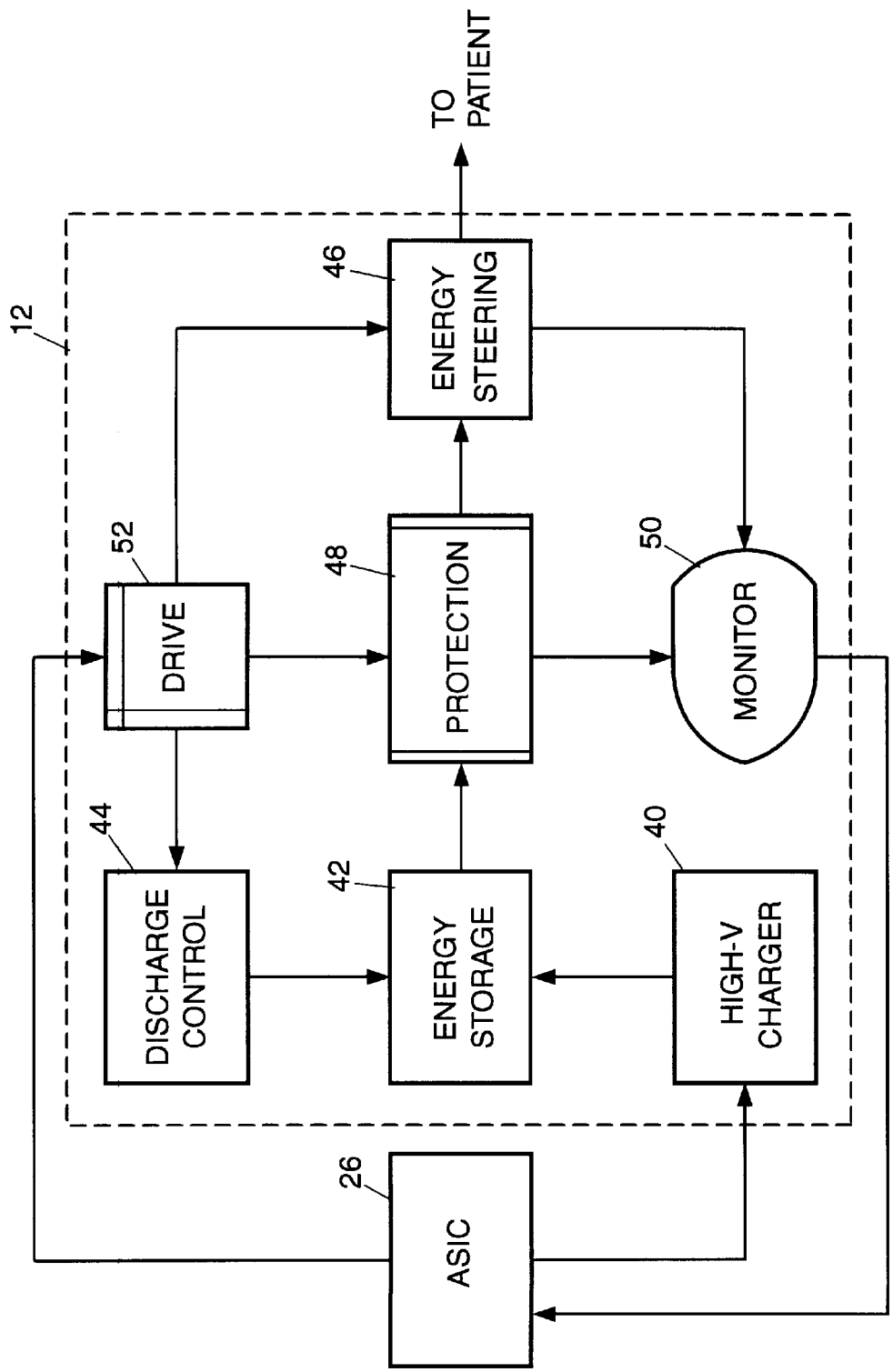
FIG. 2 is a functional block diagram depicting a high-voltage delivery circuit included in the defibrillator of FIG. 1.

As shown in FIG. 2, the high-voltage delivery circuit 12 includes a number of functional circuit blocks which are both monitored and controlled by the ASIC 26. A high-voltage charging circuit 40, such as a flyback power supply, responds to one or more control signals issued by the ASIC 26 and generates electrical energy for provision to an energy storage circuit 42. The storage circuit 42 stores the electrical energy for subsequent delivery to the patient. A discharge control circuit 44 controls discharge of the energy stored in the storage circuit 42 to an energy transfer or steering circuit 46 through a protection circuit 48. The steering circuit 46 in turn delivers the electrical energy to the patient via the connector 20 and electrodes 22 (shown in FIG. 1). The steering circuit 46 may deliver the electrical energy to the patient with a single polarity (e.g., a monophasic pulse) or with an alternating polarity (e.g., a biphasic or multiphasic pulse), as required by the desired implementation.

The protection circuit 48 functions to limit energy delivery from the storage circuit 42 to the steering circuit 46 (and hence to the patient) and to discharge or otherwise disarm the storage circuit 42 in the event of a fault condition. The protection circuit 48 operates to limit the time-rate-of-change of the current flowing through the bridge circuit. A monitor circuit 50 senses operations of both the protection circuit 48 and the steering circuit 46 and reports the results of such monitoring to the ASIC 26. The above-described operations of the discharge control circuit 44, the steering circuit 46, and the protection circuit 48 are controlled by a drive circuit 52 issuing a plurality of drive signals. Operation of the drive circuit 52 is, in turn, controlled by one or more control signals provided by the ASIC 26.

Figure 3:
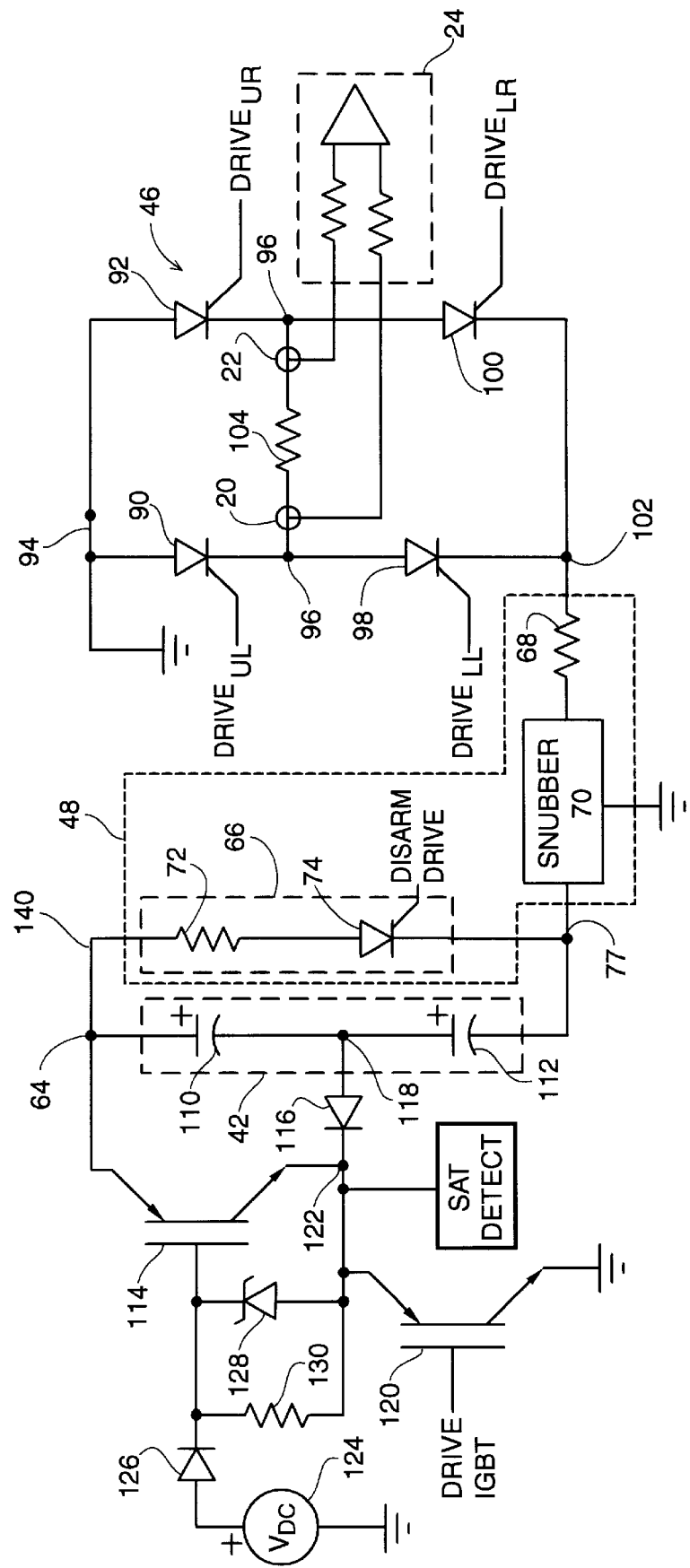
FIG. 3 is a schematic diagram depicting details of a high-voltage delivery circuit employing sequential switching of series IGBTs to get higher voltage.

In FIG. 3, the storage circuit 42 is two series-connected capacitors (or multiple capacitor units) 110, 112, with each having a suitable capacitance of approximately 200 $\mu$F and are capable of regularly and reliably storing energy at approximately 1200 V. The discharge control circuit 44 includes a series of lower voltage switching devices. As shown in FIG. 3, the lower voltage switching device is, for example, an upper IGBT 114 ("$IGBT_U$") that has its collector connected to the positive terminal of the upper capacitor 110 at node 64. The emitter of the $IGBT_U$ 114 is coupled through a diode 116 to a node 118 between the capacitors 110, 112. The discharge control circuit 44 also includes a lower IGBT 120 ("$IGBT_L$") that has its collector connected to the emitter of $IGBT_U$ 114 and the cathode of the diode 116 at a node 122. The emitter of $IGBT_L$ 120 is connected to ground potential.

The control terminal or gate of $IGBT_L$ 120 receives an IGBT drive signal produced by the drive circuit 52 (shown in FIG. 2) to selectively switch $IGBT_L$ 120 on and off. A power supply 124 applies a voltage through a diode 126 to the control terminal or gate of $IGBT_U$ 114. A suitable power supply 124 could be energized by the high voltage charger 40 (shown in FIG. 2), such as by tapping a primary winding in a high voltage flyback power supply. A suitable DC voltage level provided by the power supply 124 is approximately 20 V. A voltage regulating element, such as a Zener diode 128 is coupled between the gate and the emitter of $IGBT_U$ 114, to prevent any unduly elevated potential differences. A resistor 130 is also connected between the gate and the emitter of $IGBT_U$ 114 to enforce the switching off of $IGBT_U$. A suitable choice for each of the diodes 116 and 126 shown in FIG. 3 is a N25FG diode. A suitable choice for the Zener diode 128 is an SM8J20A diode, and a suitable resistance value for the resistor 130 is approximately 100$\Omega$.

The advantage of using a collection of lower voltage switching device, such as an IGBT, is that a collection of widely available switching devices, which have a higher on/off responsiveness, can be used to deliver a high-voltage pulse. Furthermore, the voltage rating of the switching device can have a lower overall rating than the overall voltage delivered by the defibrillator.

The protection circuit 48 of FIG. 2 is shown as three distinct subcircuits—namely, a disarm circuit 66, a protection resistor 68, and a snubber circuit 70. The disarm circuit 66 includes disarm resistor 72 (with a suitable resistance value being approximately 10$\Omega$) and a silicon-controlled rectifier switch (SCR) 74. The disarm resistor 72 and SCR 74 are connected in series between the positive terminal 64 and a negative terminal or node 77 of the energy storage circuit 42. If a fault condition is detected, the disarm SCR 74 can be switched on and the energy stored in the energy storage circuit 42 substantially dissipated in the disarm resistor 72. The disarm SCR 74 is selectively switched on by a disarm signal drive provided by the drive circuitry 52 (shown in FIG. 2).

The protection resistor 68 is in series with the snubber circuit 70 between node 77 and node 102. The protection resistor 68 limits maximum current flow, with a suitable resistance value being in the range of approximately 3–5$\Omega$. The currents associated with patient defibrillation are such that a significantly smaller resistor is desirable for current monitoring. For example, the monitor circuitry 50 (FIG. 2) could monitor the voltage drop across a 0.05$\Omega$ resistor (not shown) during patient defibrillation to provide information to the ASIC 26 concerning defibrillation current.

Operation of the snubber circuit 70 is described in more detail in co-pending application Ser. No. 09/239,408, the specification of which is incorporated herein.

The energy steering circuit 46 is of an "H-bridge" configuration, with four switching elements. The steering circuit 46 includes an upper-left (UL) switching element, such as $SCR_{UL}$ 90, and an upper-right (UR) switching element, such as SCR$_{UR}$ 92. The anode of each of SCR$_{UL}$ 90 and SCR$_{UR}$, 92 is connected to a reference voltage source, such as ground potential, in series with R$_{SHUNT}$ at an upper terminal or node 94. The cathode of each of SCR$_{UR}$ 90 and SCR$_{UL}$ 92 is connected to a respective one of two patient terminals 96 (which, in turn, are coupled with the connector 20 and a respective electrode 22 of FIG. 1). The control terminal or gate of each of SCR$_{UR}$ 90 and SCR$_{UR}$ 92 receives an UL or UR drive signal produced by the drive circuit 52 (shown in FIG. 2) to selectively switch the SCRs on. A patient is represented by a resistor 104, shown in the electrical location of the patient during circuit operation. Additionally, a functional block representation of a portion of the ECG circuitry 24 of FIG. 1 is depicted.

The steering circuit 46 also includes a lower-left (LL) switching element, such as SCR$_{LL}$ 98, and a lower-right (LR) switching element, such as SCR$_{LR}$ 100. The anode of each of SCR$_{LL}$ 98 and SCR$_{LR}$ 100 is connected to one of the patient terminals 96. The cathode of each of SCR$_{LL}$ 98 and SCR$_{LR}$ 100 is connected to a lower terminal or node 102. The control terminal or gate of each of SCR$_{LL}$ 98 and SCR$_{LR}$ 100 receives a LL or LR drive signal from the drive circuit 52 (shown in FIG. 2) to selectively switch the SCRs on. As desired, the monitor circuitry 50 of FIG. 2 can advantageously sense the voltage of the node 102 and provide such information to the ASIC 26. Alternatively, time integration of monitored current flow can provide information corresponding to voltages during patient defibrillation.

The above-described control signals applied to the gates of the SCRs 90, 92, 98, 100 may each be suitably provided by a corresponding pulse transformer. The secondary coil of each of the transformers may be tied directly to the corresponding SCR gate, with the SCRs designed so that, once triggered and conducting, they will tolerate the short-circuit on the gate-cathode junction that occurs with transformer saturation.

The SCRs 90, 92, 98, 100 are preferably not of the type commonly used in power supplies or motor control, in which switching efficiency parameters such as forward voltage drop, fast switching times, reduced current tails, average current capability, average power dissipation, etc. are considered important. In implementations according to the present invention, such traditionally "good" parameters may be undesirable. For example, fast switching times can cause ground-bounce effects, which cause difficulties in control circuit design. The SCRs 90, 92, 98, 100 are used primarily to steer current, and do not experience the power dissipation associated with more conventional switching applications of SCRs. The SCRs 90, 92, 98, 100 steer a current pulse, and their ability to handle very low duty cycle transients is more important than average power dissipation efficiencies. Accordingly, conventional SCR design rules may be relaxed or otherwise modified, such as by allowing considerably lighter semiconductor doping levels, as will be understood by those skilled in the art.

A variety of SCRs are suitable for use in this application provided the SCR has a 2500 V forward and reverse blocking voltage. Those skilled in the art will readily understand, however, that circuits may be constructed according to the present invention with components having other, suitably matched device parameters.

The operation of the circuit structure shown in FIG. 3 will now be described. The storage circuit 42 is charged by charging circuitry 40 (shown in FIG. 2), to, for example, approximately 2000 V. The voltage at the node 118 between the capacitors 110, 112 is approximately 1000 V. Correspondingly, the voltage at the node 122 and at the gate of the upper IGBT 114 are each approximately 1000 V, with the diode 126 then being reverse biased. Current conduction through the steering circuit 46 and the patient 104 is initiated by switching on IGBT$_L$ 120, connecting the node 122 to ground potential. This pulls the voltage of the node 118 between the capacitors 110, 112 to approximately ground, thereby pulling the voltage of terminal 77 of the storage circuit 42 below ground. With the voltage of the node 122 now being essentially at ground, the diode 126 is forward biased and the power supply 124 applies its voltage to the gate of IGBT$_U$ 114. Correspondingly, the positive terminal 64 of the storage circuit 42 is then coupled to ground potential, thereby lowering the voltage of node 118 below ground (and reverse biasing the diode 116) and further lowering the voltage of the negative terminal 76 below ground.

To commutate or otherwise interrupt current flow through the bridge circuit 46 in the patient 104, IGBT$_L$ 120 is turned off. The voltage at the node 122 and at the gate of IGBT$_U$ 114 then rises until the diode 126 is reverse biased, with the resistor 130 then coupling the gate and emitter of IGBT$_U$ to turn it off.

Suitable IGBTs 114, 120 may be those currently readily available 1200 V IGBTs. IGBT$_L$ 120 is suitably driven by an IGBT drive signal of approximately 10 V—a drive signal amplitude at which certain desired short circuit performance characteristics are guaranteed. In the event of a short circuit, a saturation detector coupled to node 122 will detect any unexpectedly large voltage drop across IGBT$_L$ 120 to correspondingly initiate (after elapse of a predetermined time interval, such as 10 μs) the above-described operations to disarm the storage circuit 42.

Those skilled in the art will appreciate that many of the advantages associated with the circuits described above in connection with FIG. 3 may be provided by other circuit configurations. In particular, the storage circuit 42, the discharge control circuit 44, and the steering circuit 46 are substantially connected in series, and alternative ordering of these units may be found in other embodiments of the present invention.

It will be appreciated that, while specific embodiments of the invention have been described herein for purposes of illustration, various modifications may be made without deviating from the spirit and scope of the invention. Those skilled in the art will understand that a number of suitable circuits, other than those particular ones described above, can be adapted to implement a high voltage delivery circuit in accordance with the present invention. Accordingly, the invention is not limited by the disclosed embodiments, but instead the scope of the invention is determined by the following claims.

What is claimed is:

1. A high voltage delivery circuit for producing a high voltage electrical pulse for defibrillating a patient, the high voltage delivery circuit comprising:

a steering circuit coupleable with the patient and operable to deliver the electrical pulse thereto;

a storage circuit coupled to the steering circuit and operable to deliver electrical energy to the steering circuit for delivery to the patient, the storage circuit further coupled to a charging circuit at a third node, the charging circuit for providing electrical energy to the storage circuit for storage therein; and a discharge control circuit coupled with the storage circuit and the discharge control circuit includes lower voltage switching devices to control the high voltage delivery.

2. A high voltage delivery circuit according to claim 1 wherein the steering circuit is connected to a first reference voltage at a first node and the storage circuit is coupled to the steering circuit at a second node.

3. A high voltage delivery circuit according to claim 2 wherein the discharge control circuit couples the storage circuit to a second reference voltage.

4. A high voltage delivery circuit according to claim 3 wherein the storage circuit includes a plurality of capacitors, wherein the discharge control circuit includes a plurality of IGBTs coupling the capacitors with the second reference voltage.

5. A high voltage delivery circuit according to claim 4 wherein the first and second reference voltages are substantially the same.

6. A high voltage delivery circuit according to claim 4 wherein at least one of the first and second reference voltages is ground potential.

7. A high voltage delivery circuit according to claim 1 wherein the steering circuit is operable to deliver the electrical pulse as a biphasic pulse.

* * * * *